United States Patent
Peffly et al.

(10) Patent No.: US 8,147,812 B2
(45) Date of Patent: Apr. 3, 2012

(54) PERSONAL CARE COMPOSITION COMPRISING A SILICONE ELASTOMER

(75) Inventors: Marjorie Mossman Peffly, Cincinnati, OH (US); Nicole Alane Hall, Ft. Thomas, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 148 days.

(21) Appl. No.: 11/962,167

(22) Filed: Dec. 21, 2007

(65) Prior Publication Data
US 2008/0206185 A1 Aug. 28, 2008

Related U.S. Application Data

(60) Provisional application No. 60/876,405, filed on Dec. 21, 2006.

(51) Int. Cl.
*A61Q 5/12* (2006.01)
*A61K 8/73* (2006.01)
*C08F 283/00* (2006.01)
*C08F 283/12* (2006.01)

(52) U.S. Cl. ................ 424/70.12; 424/70.13; 525/479

(58) Field of Classification Search .............. 424/70.12, 424/70.13; 525/479
See application file for complete search history.

(56) References Cited

U.S. PATENT DOCUMENTS

| | | | | |
|---|---|---|---|---|
| 5,654,362 A * | 8/1997 | Schulz et al. | | 524/862 |
| 5,889,108 A | 3/1999 | Zhang | | |
| 5,972,356 A * | 10/1999 | Peffly et al. | | 424/401 |
| 5,977,036 A * | 11/1999 | Guskey | | 510/121 |
| 5,985,294 A * | 11/1999 | Peffly | | 424/401 |
| 6,060,044 A * | 5/2000 | Cretois et al. | | 424/70.12 |
| 6,093,410 A * | 7/2000 | Peffly et al. | | 424/401 |
| 6,149,898 A * | 11/2000 | Peffly et al. | | 424/70.12 |
| 6,277,893 B1 * | 8/2001 | Babenko | | 516/67 |
| 6,316,545 B1 * | 11/2001 | Sakuta | | 524/837 |
| 6,617,446 B1 * | 9/2003 | Papadopoulos et al. | | 536/102 |
| 6,649,155 B1 * | 11/2003 | Dunlop et al. | | 424/70.27 |
| 6,930,078 B2 * | 8/2005 | Wells et al. | | 510/121 |
| 7,404,966 B2 | 7/2008 | Vatter | | |
| 2002/0012646 A1 * | 1/2002 | Royce et al. | | 424/70.11 |
| 2002/0197226 A1 * | 12/2002 | Giroud et al. | | 424/70.12 |
| 2003/0049212 A1 * | 3/2003 | Robinson et al. | | 424/59 |
| 2004/0126349 A1 * | 7/2004 | Anderson et al. | | 424/70.12 |
| 2004/0146475 A1 * | 7/2004 | Peffly et al. | | 424/70.13 |
| 2004/0234478 A1 * | 11/2004 | Clapp et al. | | 424/70.12 |
| 2004/0234483 A1 * | 11/2004 | Peffly et al. | | 424/70.13 |
| 2004/0234484 A1 * | 11/2004 | Peffly et al. | | 424/70.13 |
| 2004/0247550 A1 * | 12/2004 | Asari et al. | | 424/70.12 |
| 2004/0253197 A1 * | 12/2004 | Sakuta | | 424/70.12 |
| 2005/0026794 A1 * | 2/2005 | Utz et al. | | 510/130 |
| 2005/0158266 A1 * | 7/2005 | Peffly et al. | | 424/70.12 |
| 2006/0002880 A1 * | 1/2006 | Peffly et al. | | 424/70.13 |
| 2006/0099167 A1 * | 5/2006 | Staudigel et al. | | 424/70.13 |
| 2006/0269501 A1 * | 11/2006 | Johnson et al. | | 424/70.13 |
| 2006/0269502 A1 * | 11/2006 | Johnson et al. | | 424/70.13 |
| 2007/0110696 A1 * | 5/2007 | Johnson et al. | | 424/70.13 |
| 2007/0160555 A1 * | 7/2007 | Staudigel et al. | | 424/70.13 |
| 2007/0196309 A1 * | 8/2007 | Tarletsky et al. | | 424/70.12 |
| 2007/0258918 A1 * | 11/2007 | Modi | | 424/59 |
| 2007/0292380 A1 * | 12/2007 | Staudigel et al. | | 424/70.13 |
| 2007/0297997 A1 * | 12/2007 | Tanner | | 424/59 |
| 2008/0095731 A1 * | 4/2008 | Mitra | | 424/70.13 |
| 2008/0139432 A1 * | 6/2008 | Peffly et al. | | 510/122 |
| 2008/0206176 A1 * | 8/2008 | Peffly et al. | | 424/70.11 |
| 2008/0206179 A1 * | 8/2008 | Peffly et al. | | 424/70.13 |
| 2008/0233076 A1 * | 9/2008 | Hansenne et al. | | 424/78.03 |
| 2008/0292573 A1 * | 11/2008 | Giroud | | 424/70.12 |
| 2008/0311060 A1 * | 12/2008 | Sakuta et al. | | 424/59 |

FOREIGN PATENT DOCUMENTS
EP 1384467 B1 5/2007
* cited by examiner

*Primary Examiner* — Liam Heincer
(74) *Attorney, Agent, or Firm* — Carl J. Roof; Angela K. Haughey

(57) ABSTRACT

The present invention is directed to a personal care composition comprising:
a.) from about 5 wt. % to about 50 wt. % of a detersive surfactant;
b.) a silicone elastomer formed from the following reaction:

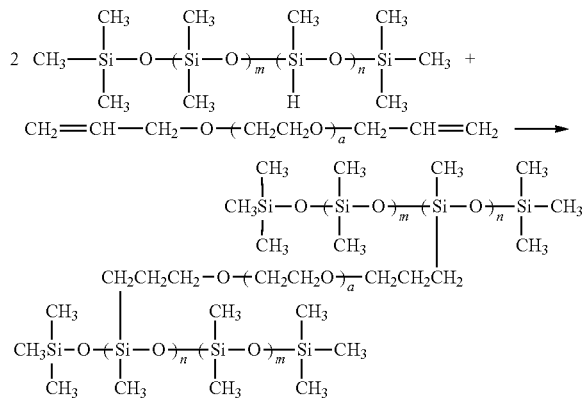

and;
c.) an aqueous carrier.
wherein m=30 to 70, n=1 to 5, and a=8 to 20.

11 Claims, No Drawings

PERSONAL CARE COMPOSITION COMPRISING A SILICONE ELASTOMER

CROSS REFERENCE TO RELATED APPLICATION

This application claims the benefit of U.S. Provisional Application Ser. No. 60/876,405 filed Dec. 21, 2006.

FIELD OF THE INVENTION

The present invention relates to personal care compositions containing combinations of hair conditioning agents and a silicone elastomer component, which provide a hair conditioning benefit.

BACKGROUND OF THE INVENTION

Silicone fluids are known additives for personal care products. Silicone fluids such as dimethicone and cyclomethicone provide hair feel and conditioning benefits in personal care compositions. Physical properties of silicone fluid polymers, including viscosity and solubility, are typically determined by molecular weight.

Unlike silicone fluids, silicone elastomers are cross-linked. The creation of cross-linkages between linear polymers, such as dimethicone, converts the linear polymer into a silicone elastomer. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions.

Typical silicone elastomers are swollen in cyclic or low molecular weight silicone fluids. Elastomers have historically been created using two different processes, suspension or solvent polymerization. In the suspension process, an initiator and cross-linking agent are added to an emulsion of the pre-cursor silicone polymer and surfactant to begin the cross-linking. Heating of the suspension drives the reaction to completion and the small dispersed droplets of precursor polymer become spherical elastomer particles. The resulting elastomer may then be spray-dried and sold as a powder or used in the emulsified form which is typically less than five microns.

The powder must be swollen in a suitable low molecular weight solvent (typically <1000 cs) before use. In the solvent process, the pre-cursor silicone polymer is solubilized, then is cross-linked by catalyst addition and a cross-linking agent. Solvents for this process are generally cylcomethicones but may also include low viscosity dimethicones or organic solvents (typically <1000 cs). The resulting gel is then broken into small particles which may be sold as a paste.

In both processes, low molecular weight or cyclic silicones are necessary for swelling the particles or for the actual cross-linking process (New Developments in Silicone Elastomers for Skin Care, M. Starch.) In aqueous shampoo applications, quantities of low molecular weight or cyclic silicones results in disruption of surfactant packing and significant decrease in both lather amount and overall viscosity. Therefore, known silicone elastomers are not well-suited for many personal care compositions, especially those that rely on surfactant structuring to achieve viscosity targets.

Based on the foregoing, there is a need for a silicone elastomer which maintains the stability and performance (i.e. does not disrupt packaging, appearance, or lather) of personal compositions.

SUMMARY OF THE INVENTION

The present invention is directed to a personal care composition comprising:

a.) from about 5 wt. % to about 50 wt. % of a detersive surfactant;

b.) a silicone elastomer formed from the following reaction:

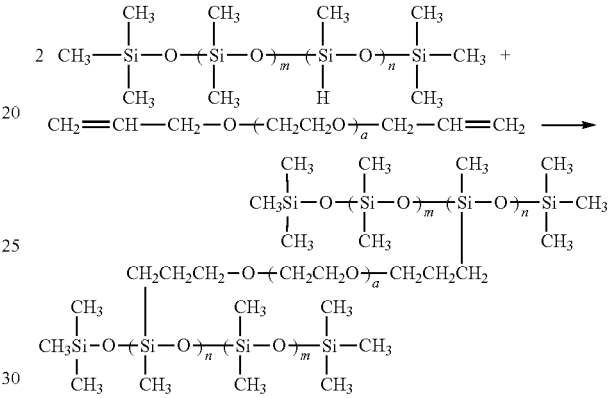

and;

c.) an aqueous carrier.

wherein m=30 to 70, n=1 to 5, and a=8 to 20.

These and other features, aspects, and advantages of the present invention will become evident to those skilled in the art from reading the present disclosure.

DETAILED DESCRIPTION OF THE INVENTION

While the specification concludes with claims that particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level, and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

All ratios are weight ratios unless specifically stated otherwise.

The term "silicone elastomer gel", as used herein, means a substance formed from the reaction between an organohydrogen polysiloxane and a dimethylpolysiloxane as described herein. This term is considered to be synonymous with "silicone elastomer" and "elastomer" herein.

Herein, "cs" means centistoke.

Herein, "molecular weight" is measured in terms of the weight average molecular weight, and is measured by gel permeation chromatography (GPC).

The term "galactomannan polymer derivative", means a compound obtained from a galactomannan polymer (i.e. a galactomannan gum).

The term "water-soluble," as used herein, means that the polymer is soluble in water in the present composition. In general, the polymer should be soluble at 25° C. at a concentration of at least 0.1% by weight of the water solvent, preferably at least 1%, more preferably at least 5%, most preferably at least 15%.

The term "water-insoluble," as used herein, means that a compound is not soluble in water in the present composition. Thus, the compound is not miscible with water.

Detersive Surfactant

The personal care composition of the present invention includes a detersive surfactant. The detersive surfactant is included to provide cleaning performance to the composition. The detersive surfactant may be selected from the group consisting of anionic detersive surfactants, zwitterionic or amphoteric detersive surfactants, and combinations thereof. Such surfactants should be physically and chemically compatible with the essential components described herein, or should not otherwise unduly impair product stability, aesthetics or performance.

Suitable anionic detersive surfactants for use in the personal care composition include those which are known for use in hair care or other personal care cleansing compositions. The concentration of the anionic surfactant component in the composition should be sufficient to provide the desired cleaning and lather performance, and generally range from about 5% to about 50%, preferably from about 8% to about 30%, more preferably from about 10% to about 25%, even more preferably from about 12% to about 22%.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Concentrations of such amphoteric detersive surfactants preferably ranges from about 0.5% to about 20%, preferably from about 1% to about 10%. Non-limiting examples of suitable zwitterionic or amphoteric surfactants are described in U.S. Pat. Nos. 5,104,646 (Bolich Jr. et al.), and 5,106,609 (Bolich Jr. et al.).

Silicone Elastomer Gel

The personal care compositions of the present invention comprise a silicone elastomer gel formed from the following reaction:

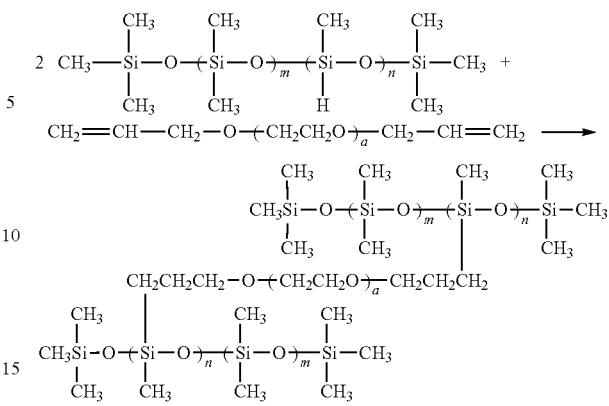

wherein m=30 to 70, n=1 to 5, and a=8 to 20.

The silicone elastomer gel component is present in the personal care composition to provide conditioning and feel benefits. Specifically, when present in a hair care composition, the silicone elastomer gel provides wet hair feel and conditioning benefits. Additionally, the silicone elastomer gel has surprisingly been found not to significantly disrupt or interfere with the stability and performance of personal compositions to which it is added.

The silicone elastomer gel is present in the personal care compositions herein in the amount of from about 0.01% to about 10% by weight, more preferably from about 0.1% to about 1% by weight, and most preferably from about 0.1% to about 1.0% by weight of the personal care composition. For this reason, the preferred elastomeric material is one in which the swelling fluid viscosity is between 1,250-750,000 cs and where the cross-linking of the pre-cursor polymer is performed in the presence of this swelling fluid.

A detailed description of the above reaction is found in U.S. Patent Publication 2004/0253197 to Sakuta.

In a preferred embodiment, the silicone elastomer gel is incorporated into a shampoo composition. In order to incorporate the silicone elastomer in to a shampoo system, a separate emulsion is first formed, before the elastomer is added to the shampoo system. The elastomer and higher viscosity silicone fluid are blended until homogenous. Following homogenization, the blend is emulsified into large particles using a surfactant, salt, and water. The most relevant variables for achieving the large particle emulsion include mixing speed, mixing time, ratio of the silicone blend in the final formula, and viscosity of the external phase. The higher the shear rate as induced by mixing speed and viscosity of the external phase, the smaller the particle size. Increased mixing times can also decrease particle sizes. The emulsion is then added to the full shampoo formula at the end of the batch and under low shear conditions so as not to alter the particle size significantly on addition to the shampoo. For a smaller particle elastomer-only emulsion, mixing speed, mixing time, ratio of silicone elastomer in the final formula, and co-surfactant type are the determinative parameters. The elastomer emulsion is introduced to the shampoo in the same manner as the silicone/elastomer blend emulsion described above. This introduction into the shampoo may be done alone or in conjunction with a separate large particle dimethicone emulsion. The remainder of the batch is made with standard shampoo making technology.

Aqueous Carrier

Preferred embodiments of the present invention are in the form of pourable liquids (under ambient conditions). Such compositions will therefore typically comprise an aqueous carrier, which is present at a level of from about 20% to about 95%, more preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

Cationic Polymers

The personal care composition of the present invention may also comprise one or more cationic polymers which function as a deposition aid of conditioning agents.

In order to adjust rinse feel for specific consumer groups, one embodiment of the present invention comprises blends of the silicone elastomer with cationic polymers selected from cationic celluloses, cationic guars, cationic starches, non-guar galactomannans, synthetic polymers and mixtures thereof. Each of the cationic polymers, described herein, aid in deposition of conditioning agents to skin or hair.

Cellulose or Guar Cationic Deposition Polymers

The personal care compositions of the present invention may include cellulose or guar cationic deposition polymers. Generally, such cellulose or guar cationic deposition polymers may be present at a concentration from about 0.05% to about 5%, by weight of the composition. Suitable cellulose or guar cationic deposition polymers have a molecular weight of greater than about 5,000. Additionally, such cellulose or guar deposition polymers have a charge density from about 0.5 meq/g to about 4.0 meq/g at the pH of intended use of the personal care composition, which pH will generally range from about pH 3 to about pH 9, preferably between about pH 4 and about pH 8. The pH of the compositions of the present invention are measured neat.

Suitable cellulose or guar cationic polymers include those which conform to the following formula:

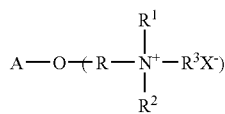

wherein A is an anhydroglucose residual group, such as a cellulose anhydroglucose residual; R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion. Non-limiting examples of such counterions include halides (e.g., chlorine, fluorine, bromine, iodine), sulfate and methylsulfate. The degree of cationic substitution in these polysaccharide polymers is typically from about 0.01 to about 1 cationic groups per anhydroglucose unit.

In one embodiment of the invention, the cellulose or guar cationic polymers are salts of hydroxyethyl cellulose reacted with trimethyl ammonium substituted epoxide, referred to in the industry (CTFA) as Polyquaternium 10 and available from Amerchol Corp. (Edison, N.J., USA).

Cationically Modified Starch Polymer

In one embodiment, the personal care compositions further comprise water-soluble cationically modified starch polymers. As used herein, the term "cationically modified starch" refers to a starch to which a cationic group is added prior to degradation of the starch to a smaller molecular weight, or to a starch to which a cationic group is added after modification of the starch to a desired molecular weight. The definition of the term "cationically modified starch" also includes amphoterically modified starch. The term "amphoterically modified starch" refers to a starch hydrolysate to which a cationic group and an anionic group are added.

In one embodiment, the personal care compositions comprise cationically modified starch polymers at a range of about 0.01% to about 10%, and more preferably from about 0.05% to about 5%, by weight of the composition.

The cationically modified starch polymers suitable for use in the personal care compositions of the present invention have a molecular weight from about 1,000 to about 200,000. In one embodiment of the present invention, the cationically modified starch polymers have a molecular weight from about 5,000 to about 100,000. The weight average molecular weight may be measured by gel permeation chromatography ("GPC") using an Alliance HPLC (Waters 2695 Separation Module) with two hydrogel columns in series (Waters Ultrahydrogel Linear 6-13 um, 7.8×300 nm GPC column, part number 011545) at a column temperature of 30° C. and at a flow rate of 0.9 ml/min, and using a Viscotek Model 300 TDA (triple detector array), light scattering detector (single angle, 90°), viscosity detector, and refractive index detector, all at detector temperatures of 30° C., with a method created by using pullulan narrow standard P-800 from American Polymer Standards Corporation ($M_w$=788,000), with an injection volume of 25 to 100 μl, and using a dn/dc of 0.147. Additional details on measuring the weight average molecular weight according to a GPC method are described in U.S. Patent Publication No. 2003/0154883 A1, entitled "Non-Thermoplastic Starch Fibers and Starch Composition for Making Same."

In one embodiment, the personal care compositions of the present invention include cationically modified starch polymers which have a charge density from about 0.7 meq/g to about 7 meq/g. The chemical modification to obtain such a charge density includes, but is not limited to, the addition of amino and/or ammonium groups into the starch molecules. Preferably, the cationic starch is derived from waxy corn starch.

Non-limiting examples of suitable cationically modified starch polymers are described in U.S. patent application Publication U.S. Ser. No. 10/758,656 to Peffly et al.

Non-Guar Galactomannan Polymer

In one embodiment, the second non-guar cationic polymer is a non-guar galactomannan polymer derivative having a mannose to galactose ratio of greater than 2:1 on a monomer to monomer basis, the non-guar galactomannan polymer derivative selected from the group consisting of a cationic non-guar galactomannan polymer derivative and an amphoteric non-guar galactomannan polymer derivative having a net positive charge. As used herein, the term "cationic non-guar galactomannan" refers to a non-guar galactomannan polymer to which a cationic group is added. The term "amphoteric non-guar galactomannan" refers to a non-guar galactomannan polymer to which a cationic group and an anionic group are added such that the polymer has a net positive charge.

Non-guar galactomannan polymers are present in the endosperm of seeds of the Leguminosae family. Non-guar galactomannan polymers are made up of a combination of mannose monomers and galactose monomers. The non-guar galactomannan molecule is a straight chain mannan branched at regular intervals with single membered galactose units on specific mannose units. The mannose units are linked to each other by means of 0 (1-4) glycosidic linkages. The galactose branching arises by way of an α (1-6) linkage. The ratio of mannose monomers to galactose monomers varies according to the species of the plant and also is affected by climate. Non-guar galactomannan polymers of the present invention have a ratio of mannose to galactose of greater than 2:1 on a monomer to monomer basis (i.e., non-guar galactomannan polymers). Preferably, the ratio of mannose to galactose is greater than about 3:1, and more preferably the ratio of mannose to galactose is greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and Cassia gum (5 parts mannose/1 part galactose).

The non-guar galactomannan polymer derivatives for use in the personal care compositions of the present invention have a molecular weight from about 1,000 to about 10,000,000. In one embodiment of the present invention, the non-guar galactomannan polymer derivatives have a molecular weight from about 5,000 to about 3,000,000. As used herein, the term "molecular weight" refers to the weight average molecular weight. The weight average molecular weight may be measured by gel permeation chromatography.

The non-guar galactomannan polymer derivatives have a cationic charge density from about 0.7 meq/g to about 7 meq/g. In one embodiment of the present invention, the non-guar galactomannan polymer derivatives have a charge density from about 0.9 meq/g to about 7 meq/g. The degree of substitution of the cationic groups onto the non-guar galactomannan structure should be sufficient to provide the requisite cationic charge density.

Other Cationic Deposition Polymers

The personal care compositions of the present invention may also include synthetic cationic deposition polymers. Generally, such synthetic cationic deposition polymers may be present at a concentration from about 0.025% to about 5%, by weight of the composition. Such synthetic cationic deposition polymers have a molecular weight from about 1,000 to about 5,000,000. Additionally, such synthetic cationic deposition polymers have a charge density from about 0.5 meq/g to about 10 meq/g.

Suitable synthetic cationic deposition polymers include those which are water-soluble or dispersible, cationic, non-crosslinked, conditioning copolymers comprising: (i) one or more cationic monomer units; and (ii) one or more nonionic monomer units or monomer units bearing a terminal negative charge; wherein said copolymer has a net positive charge, a cationic charge density of from about 0.5 meq/g to about 10 meq/g, and an average molecular weight from about 1,000 to about 5,000,000. In a preferred embodiment, at least one cationic polymer is a copolymer of Acrylamide (AM) and TRIQUAT monomers ("AM:TRIQUAT"). Such polymers are described in detail in U.S. Patent Application Ser. No. 60/774,533 to Peffly et al.

Non-limiting examples of suitable synthetic cationic deposition polymers are described in United States Patent Application Publication US 2003/0223951 A1 to Geary et al.

Oily Conditioning Agent

In yet another embodiment of the present invention, the personal care composition comprises one or more oily conditioning agents. Oily conditioning agents include materials which are used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The oily conditioning agents useful in the compositions of the present invention typically comprise a water-insoluble, water-dispersible, non-volatile, liquid that forms emulsified, liquid particles. Suitable oily conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

When present, one or more oily conditioning agents are typically present at a concentration from about 0.01% to about 10%, preferably from about 0.1% to about 8%, more preferably from about 0.2% to about 4%, by weight of the composition.

Silicone Conditioning Agent

The personal care compositions of the present invention may also comprise one or more oily conditioning agents, which is preferably a water-insoluble silicone conditioning agent. The silicone conditioning agent may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 cs, more preferably from about 1,000 to about 1,800,000 cs, even more preferably from about 5,000 to about 1,500,000 cs, more preferably from about 10,000 to about 1,000,000 cs.

Non-volatile silicone oils suitable for use in compositions of the present invention may be selected from organo-modified silicones and fluoro-modified silicones. In one embodiment of the present invention, the non-volatile silicone oil is an organo-modified silicone which comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups.

In a preferred embodiment of the present invention, the non-volatile silicone oil is dimethicone.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a.) from about 5 wt. % to about 50 wt. % of a detersive surfactant;
   b.) a silicone elastomer formed from the following reaction:

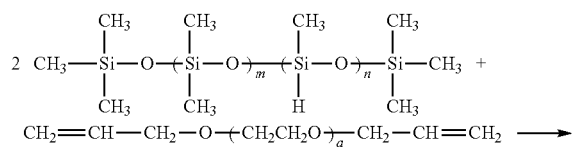

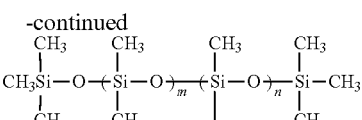

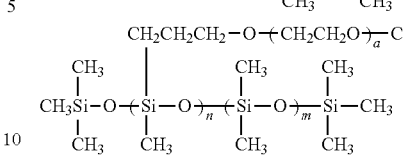

in the presence of a swelling fluid having a viscosity of 1250 to 750,000 cs;
   and;
   c.) an aqueous carrier
   wherein m=30 to 70, n=1 to 5, and a=8 to 20.

2. A composition according to claim 1, further comprising a cationic polymer.

3. A composition according to claim 1, further comprising a cationic cellulose polymer.

4. A composition according to claim 1, further comprising a cationic guar polymer.

5. A composition according to claim 1, further comprising a cationically modified starch polymer.

6. A composition according to claim 5, wherein said cationically modified starch polymer is derived from waxy corn starch.

7. A composition according to claim 1, further comprising a non-guar galactomannan polymer.

8. A composition according to claim 7, wherein said non-guar galactomannan is derived from cassia gum.

9. A composition according to claim 1, further comprising an oily conditioning agent.

10. A composition according to claim 9, wherein said oily conditioning agent is a water-insoluble silicone conditioning agent.

11. A composition according to claim 10, wherein said water-insoluble silicone conditioning agent is dimethicone.

* * * * *